(12) United States Patent
Flynn et al.

(10) Patent No.: US 7,946,288 B2
(45) Date of Patent: May 24, 2011

(54) BITE BLOCK SYSTEM AND METHOD

(75) Inventors: Marybeth Dorothy Flynn, Sarasota, FL (US); Rodolfo Diaz Prieto, Clearwater, FL (US)

(73) Assignee: Encompas Unlimited, Inc., Tallevast, FL (US)

( * ) Notice: Subject to any disclaimer, the term of this patent is extended or adjusted under 35 U.S.C. 154(b) by 1197 days.

(21) Appl. No.: 11/558,574

(22) Filed: Nov. 10, 2006

(65) Prior Publication Data
US 2008/0110456 A1 May 15, 2008

(51) Int. Cl.
| *A61M 15/00* | (2006.01) |
| *A61M 16/00* | (2006.01) |
| *A62B 7/00* | (2006.01) |
| *A62B 9/00* | (2006.01) |
| *A62B 18/00* | (2006.01) |

(52) U.S. Cl. .................. 128/200.24; 128/859; 128/861; 128/207.18; 128/207.14

(58) Field of Classification Search ............. 128/200.24, 128/200.26, 861, 859, 207.18, 912, 207.17, 128/207.14; 600/543; 73/23.3
See application file for complete search history.

(56) References Cited

U.S. PATENT DOCUMENTS

| 69,396 A | 10/1867 | Brayton et al. |
| 146,730 A | 1/1874 | Vickers |
| 718,785 A | 1/1903 | McNary |
| 1,445,010 A | 2/1923 | Feinberg |
| 2,127,215 A | 8/1938 | Gwathmey |
| 2,705,959 A | 4/1955 | Elmore |
| 2,931,358 A | 4/1960 | Sheridan |
| 3,508,543 A | 4/1970 | Aulicono |
| 3,513,844 A | 5/1970 | Smith |
| 3,643,660 A | 2/1972 | Hudson et al. |
| 3,754,552 A | 8/1973 | King |
| 3,756,244 A | 9/1973 | Kinnear et al. |
| 3,802,431 A | 4/1974 | Farr |
| 4,231,364 A | 11/1980 | Speshyock |
| 4,263,908 A | 4/1981 | Mizerak |
| 4,270,531 A | 6/1981 | Blachly et al. |
| 4,454,880 A | 6/1984 | Muto et al. |
| 4,640,273 A | 2/1987 | Greene et al. |
| 4,881,542 A | 11/1989 | Schmidt et al. |
| 4,944,313 A | 7/1990 | Katz et al. |

(Continued)

OTHER PUBLICATIONS

Capnographic-Oxygenating Oro-Fiberscopic Biteblock; Jul. 2005; Clinical Solutions International, LLC, Vernon, VT (Admitted Prior Art).

*Primary Examiner* — Justine R Yu
*Assistant Examiner* — Colin Stuart
(74) *Attorney, Agent, or Firm* — Jacox, Meckstroth & Jenkins (57) ABSTRACT

A medical apparatus that holds open a mouth of a patient. The apparatus contains a passage through which the patient can breathe by mouth. The apparatus contains a port to which an oxygen line is connected and which delivers oxygen to the passage for inhalation by the patient. The apparatus contains a sampling port which samples air in the passage and delivers sampled air to a monitoring device. The latter measures, for example, carbon dioxide content in the sampled gas, and issues a warning if carbon dioxide concentration is out-of-bounds. Phosphor material can be added to the apparatus, to make the apparatus glow in a darkened operating room, to allow technicians to easily find the patient's mouth and to insert tools, tubing, instruments and the like in the patient's mouth.

65 Claims, 7 Drawing Sheets

U.S. PATENT DOCUMENTS

| | | | |
|---|---|---|---|
| 5,046,491 A * | 9/1991 | Derrick | 128/200.24 |
| D329,901 S | 9/1992 | Jackson | |
| 5,174,284 A | 12/1992 | Jackson | |
| 5,195,513 A | 3/1993 | Sinko et al. | |
| 5,269,296 A | 12/1993 | Landis | |
| 5,273,032 A | 12/1993 | Borody | |
| D348,932 S | 7/1994 | Jackson | |
| 5,375,593 A | 12/1994 | Press | |
| 5,402,776 A | 4/1995 | Islava | |
| 5,413,095 A | 5/1995 | Weaver | |
| 5,421,327 A | 6/1995 | Flynn et al. | |
| 5,513,633 A | 5/1996 | Islava | |
| 5,513,634 A | 5/1996 | Jackson | |
| 5,572,994 A | 11/1996 | Smith | |
| 5,752,510 A | 5/1998 | Goldstein | |
| 5,857,461 A | 1/1999 | Levitsky et al. | |
| 5,975,077 A | 11/1999 | Hofstetter et al. | |
| 6,055,986 A | 5/2000 | Meade | |
| 6,186,958 B1 | 2/2001 | Katzman et al. | |
| 6,379,312 B2 | 4/2002 | O'Toole | |
| 6,422,240 B1 * | 7/2002 | Levitsky et al. | 128/207.18 |
| 6,491,643 B2 | 12/2002 | Katzman et al. | |
| 6,517,549 B1 | 2/2003 | Dennis | |
| 6,533,983 B2 | 3/2003 | Curti | |
| 6,533,984 B2 | 3/2003 | Curti | |
| 6,561,192 B2 | 5/2003 | Palmer | |
| 6,595,215 B2 | 7/2003 | Wood | |
| D479,876 S | 9/2003 | Gradon et al. | |
| 6,669,712 B1 | 12/2003 | Cardoso | |
| 6,679,257 B1 | 1/2004 | Robertson et al. | |
| 6,679,265 B2 | 1/2004 | Strickland et al. | |
| 6,758,212 B2 | 7/2004 | Swann | |
| 6,805,126 B2 | 10/2004 | Dutkiewicz | |
| 6,807,967 B2 | 10/2004 | Wood | |
| 6,810,878 B2 | 11/2004 | Palmer | |
| 6,820,617 B2 | 11/2004 | Robertson et al. | |
| 6,830,445 B2 | 12/2004 | Curti | |
| 6,863,069 B2 | 3/2005 | Wood | |
| RE38,728 E | 4/2005 | Katzman et al. | |
| D504,947 S | 5/2005 | McAuley et al. | |
| 6,926,005 B1 | 8/2005 | Colman et al. | |
| 6,997,186 B2 | 2/2006 | Robertson et al. | |
| 7,017,579 B2 | 3/2006 | Palmer | |
| 2004/0040556 A1 | 3/2004 | Fillyaw | |
| 2004/0129273 A1 | 7/2004 | Hickle | |
| 2005/0081849 A1 | 4/2005 | Warren | |
| 2005/0103347 A1 * | 5/2005 | Curti et al. | 128/207.18 |
| 2005/0273016 A1 | 12/2005 | Colman et al. | |
| 2005/0279362 A1 | 12/2005 | Colman et al. | |
| 2006/0278238 A1 * | 12/2006 | Borody | 128/848 |
| 2007/0006878 A1 | 1/2007 | Mackey et al. | |
| 2007/0009856 A1 * | 1/2007 | Jones et al. | 433/215 |
| 2007/0113844 A1 * | 5/2007 | Garren et al. | 128/200.26 |
| 2009/0275851 A1 * | 11/2009 | Colman et al. | 600/532 |

* cited by examiner

BITE BLOCK SYSTEM AND METHOD

BACKGROUND OF THE INVENTION

1. Field of the Invention

The invention concerns an appliance which comfortably holds open the mouth of a patient during a medical or surgical procedure, delivers breathable oxygen to the patient and samples carbon dioxide concentration in the air exhaled by the patient.

2. Description of the Related Art

During medical procedures, a device is sometimes used to hold open a patient's mouth while providing an airway through which the patient can breathe normally. Such devices or appliances are sometimes called endoscopic mouth guards or bite blocks. The airway also provides access for medical personnel to insert various devices, such as tubing, into the patient's mouth or throat for various purposes. This bite block facilitates protecting instruments, endoscopes, tubing, tools and the like from being bitten by the patient.

U.S. Pat. Nos. 6,926,005, RE38,728, 6,491,643, 6,422,240, 6,186,958, 5,857,461, 5,174,284, 5,513,634, 348,932, 329,901, 4,944,313, 4,640,273, and Publication numbers 2005/0279362, 2005/0273016 show various prior art devices relating to bite blocks and similar devices used in the past.

The invention offers advancements upon one or more of such devices.

SUMMARY OF THE INVENTION

An object of the invention is to provide an improved medical device or appliance which holds open a patient's mouth during medical procedures.

In one form of the invention, a mouthpiece is provided which holds open a patient's mouth, offers a passage through which the patient can breathe and through which medical devices can be inserted into the mouth and throat, delivers a stream of oxygen to the passage for the patient to breathe, and samples exhaled gases from the patient, to indicate the concentration of carbon dioxide in the patient's lungs for diagnostic purposes.

In another form, this invention comprises a medical apparatus, comprising:
a) an appliance which holds open a patient's mouth, comprising:
  i) a passage through which the patient can breathe ambient atmospheric air;
  ii) a conduit effective to deliver oxygen from an external supply to the passage, and
b) an outlet conduit which connects to the passage, and extracts some air from the passage and delivers extracted air to a gas-monitoring apparatus.

In still another form, this invention comprises a medical apparatus, comprising:
a) a body which fits into a patient's mouth and contains a passage through which the patient can breathe ambient atmospheric air;
b) a first conduit which connects the passage with an oxygen port; and
c) a second conduit which connects the passage with a sampling port.

In yet another form, this invention comprises a medical apparatus, comprising:
a) an appliance which
  i) holds open a patient's mouth, and ii) provides a passage through which the patient can breathe ambient atmospheric air normally;
b) a manifold supported by the appliance, comprising:
  i) a first set of star-connected conduits, wherein
    A) a first conduit leads to an oxygen port,
    B) a second conduit leads to the passage, and
    C) a third conduit leads to a chamber;
  ii) a second set of star-connected conduits, wherein
    A) a fourth conduit leads to a sampling port,
    B) a fifth conduit leads to the passage, and
    C) a sixth conduit leads to the chamber.

In another form this invention comprises a method, comprising:
a) maintaining a body within a patient's mouth which provides a passage through which the patient can breathe ambient atmospheric air;
b) delivering oxygen to the passage, for inhalation by the patient; and
c) sampling air in the passage, and detecting concentration of a gas in sampled air.

In yet another form this invention comprises a medical apparatus, comprising:
a) an appliance which holds open a patient's mouth, which includes a passage through which the patient can breathe ambient atmospheric air;
b) an oxygen conduit in the appliance which delivers oxygen to the patient's mouth and nose;
c) a sampling conduit which samples air exhaled by the patient, and which is positioned such that exhaled air inhibits oxygen delivered by the oxygen conduit from reaching the sampling conduit.

These and other objects and advantages of the invention will be apparent from the following description, the accompanying drawings and the appended claims.

DETAILED DESCRIPTION OF THE INVENTION

Figure 1:
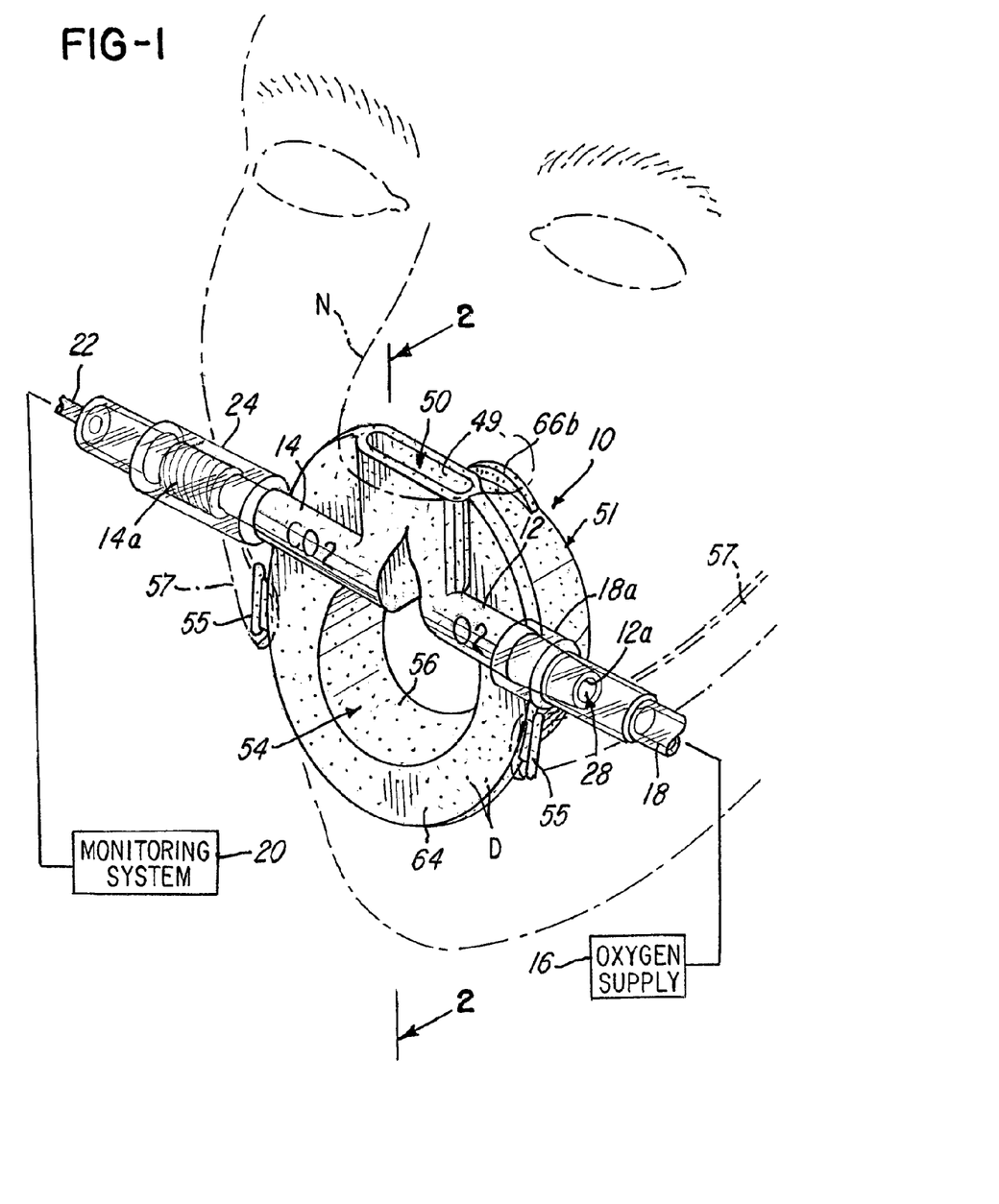
FIG. 1 illustrates one form of the invention in the form of a bite block or manifold, fastened to the face of a patient.

FIG. 1 illustrates a system for directing oxygen and providing diagnostic information relative to a patient. The system comprises a bite block, appliance, bite block, manifold or mouthpiece 10. The bite block 10 is an integral one-piece molded construction, which for ease of reference shall be referred to as bite block 10. In one embodiment, the bite block 10 is molded from a thermoplastic or polymer material, such as a polypropylene, polyethylene or other material. In one embodiment, it is preferable that the material be approved by the United States Food and Drug Administration. To produce or mold the bite block 10, a multi-cavity plastic injection mold (not shown) is used. The mold is placed in a conventional plastic injection molding press (not shown) to process. A high pressure injection of, for example, a thermoplastic material that has been melted at a high temperature is injected into the mold. Typically, the mold is cooled with cold water to cure the plastic to form the bite block 10 in approximate thirty seconds. This cycle is then repeated over and over.

The bite block 10 comprises an inlet port, connecting portion or member 12 and sampling port, outlet port, connecting portion or member 14. As illustrated in FIG. 1, the inlet port, connecting portion or member 12 is coupled to an oxygen supply 16 via an oxygen line or tubing 18 having a nipple or end portion 18a coupled to the inlet port, connecting portion or member 12 as shown. The outlet port, connecting portion or member 14 has a threaded end or coupling 15a (FIG. 4) that is connected to a monitoring system 20 via a suitable line or tubing 22 and adapted or configured to mate with a conventional quick-connect connector 24.

The oxygen line 18 originates in the oxygen supply 16 and is coupled to and in fluid communication therewith so that oxygen may be provided therefrom, through the line 18 and to an inlet, conduit or passageway 28 defined by an inlet wall 12a (FIG. 1) of the connecting portion 12. The passageway 28 directs the fluid, such as oxygen, into and through at least one or a plurality of passageways, conduits, channels or ducts 34 and 36 associated with a mouth and nose, respectively, of a patient. The passageways or channels 34 and 36 (FIG. 6) are defined by walls 38 and 40, respectively, that are integrally formed in the bite block 10. The oxygen supply 16 can take the form of an oxygen tank (not shown) to which is attached a pressure regulator (not shown), which regulates oxygen through line 18. Advantageously, the circuit of conduits and passageways 28, 34 and 36 provide a substantially constant oxygen supply to the patient's nose N and oral/throat passage.

The sampling or outlet port 14 is coupled to the tubing 22 and provides an outlet conduit or passageway 32 defined by wall 14a adapted to extract or receive fluid or fluid samples, such as $CO_2$, from the patient's nose and throat via at least one or a plurality of passageways, conduits, channels or ducts 42 and 44, described later herein relative to FIG. 5. The fluid or samples are delivered via tubing 22 to the monitoring system 20. These channels 42 and 44 are defined by walls 46 and 48, respectively, as shown, which are also integrally formed in the bite block 10. In the illustration being described, the monitoring system 20 measures carbon dioxide concentration in the samples or patient's exhale received in the line 22. Carbon dioxide monitoring systems are commercially available from manufacturers, such as Nellcor Incorporated of Pleasanton, Calif.; Welch Allyn, Inc. of Skaneateles Falls, N.Y.; and Hewlett-Packard Company of Palo Alto, Calif. For example, one monitoring system 20 may comprise the Model No HP M1026A available from Hewlett-Packard Company of Palo Alto, Calif.

Figure 4:
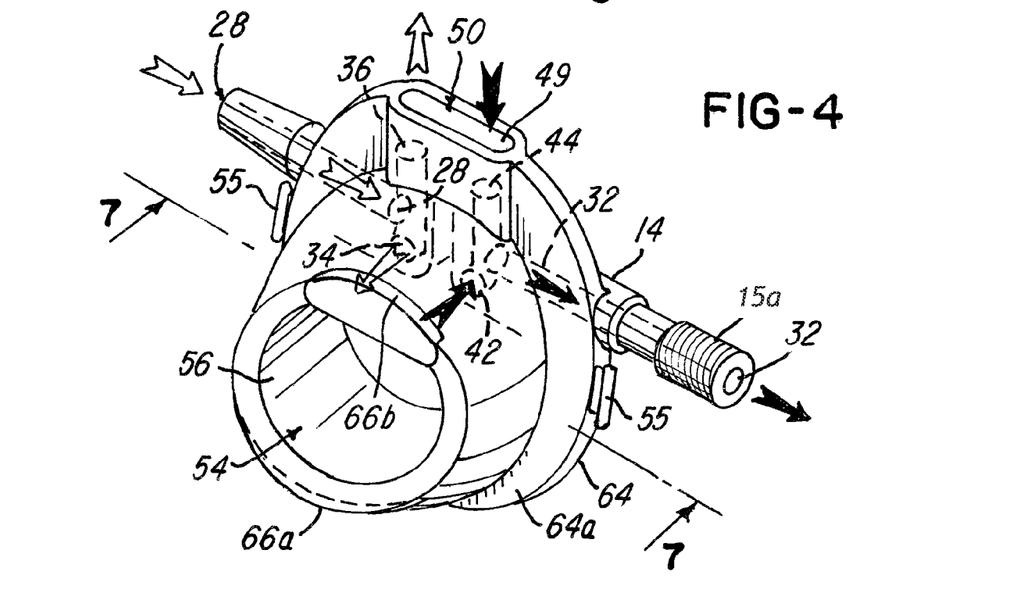
FIG. 4 is a perspective view of the device of FIG. 1, viewed from the rear of the device which is placed inside the mouth of the patient.

Another feature of the illustrative embodiment, as shown in FIG. 1, is that the inlet port 12 and outlet port 14 have indicia applied thereto, embossed or integrally molded therein that indicates the fluid ("$O_2$" and "$CO_2$" in the illustration being described) to be received in the inlet passageway 28 and outlet passageway 32 (FIG. 4).

Figure 2:
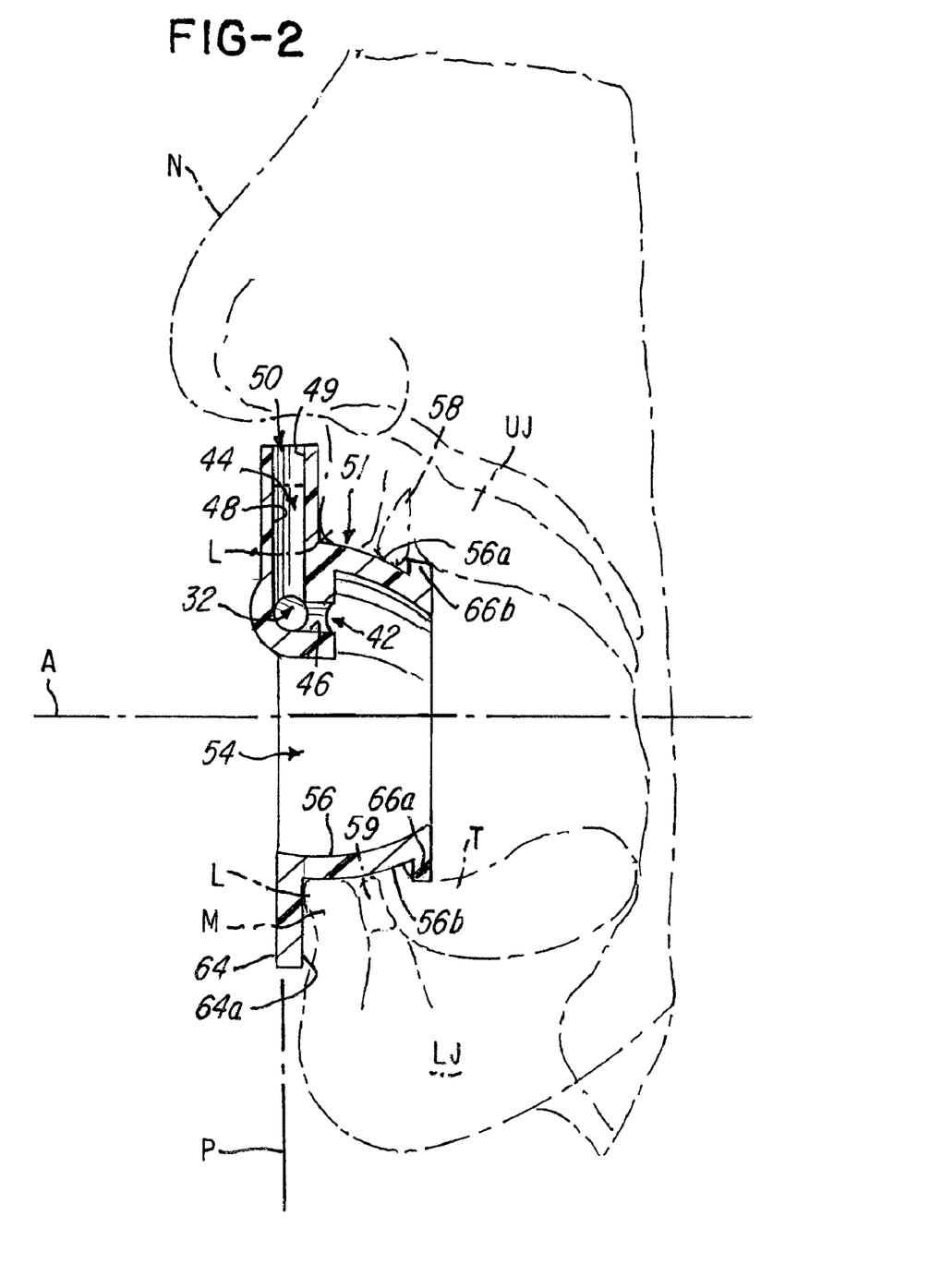
FIG. 2 is a cross-sectional view of the device of FIG. 1 taken along the line 2-2 in FIG. 1.
Figure 3:
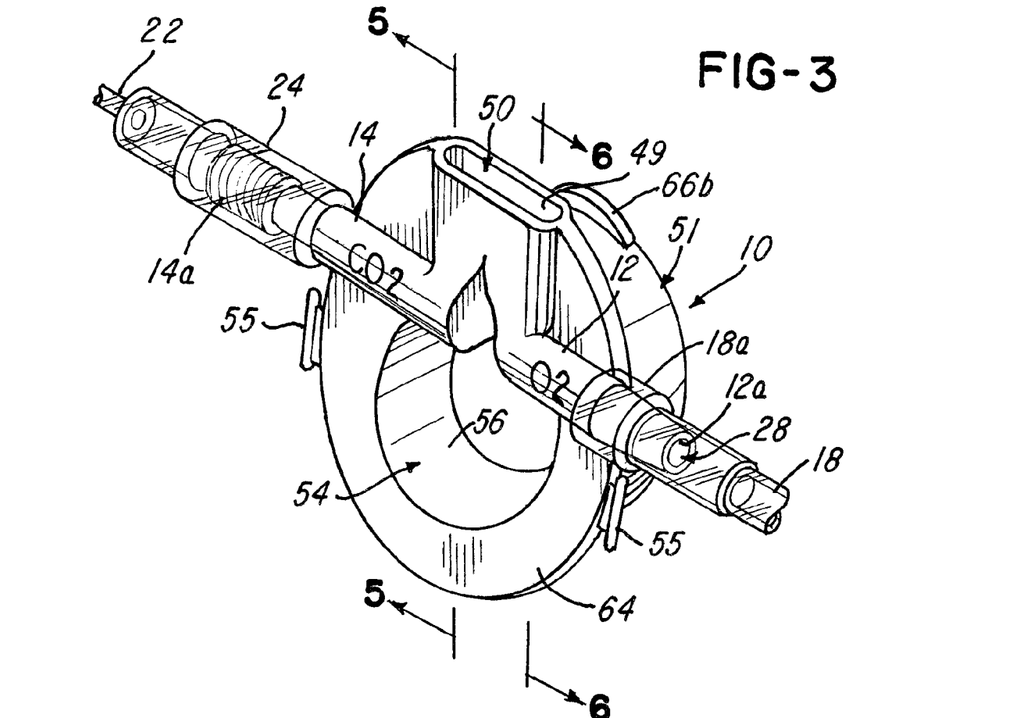
FIG. 3 is a perspective view of the device of FIG. 1, viewed from a front of the device, that is, viewed by a person facing the patient.

As shown in FIG. 2, the bite block 10 contains a generally cylindrical, curved or an annular body 51 which comprises a wall 56 that defines or surrounds the internal air or primary passageway 54. In one illustration, the wall 56 comprises a general diameter of about 22 millimeters for ease of instrument access, tool or tubing insertion and the like. For example, in the illustration, the primary passageway 54 is adapted to receive a number 60 esophageal dilator.

Figure 5:
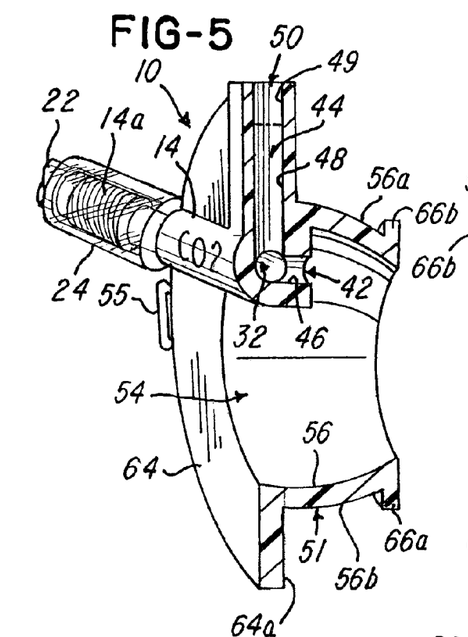
FIG. 5 is a sectional perspective view of the device of FIG. 3, viewed in the direction of line 5-5 point in FIG. 3.
Figure 6:
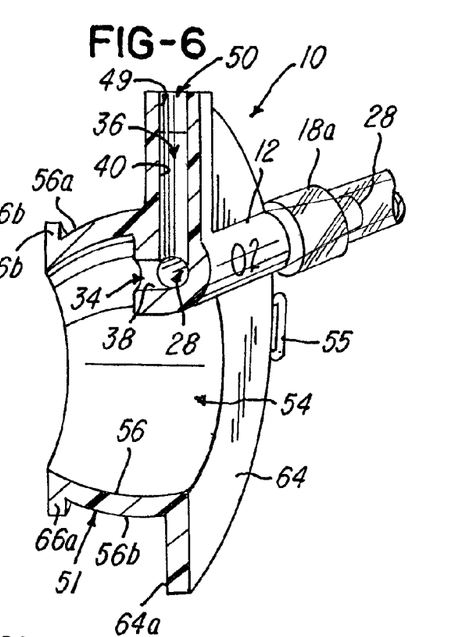
FIG. 6 is a sectional perspective view of the device of FIG. 3, viewed in the direction of line 6-6 point in FIG. 3.

Notice in FIGS. 2, 5 and 6 that the bite block 10 comprises an oval-shaped wall 49 that extends radially away from an axis A (FIG. 2). The wall 49 defines a common opening, aperture or area 50 that defines or provides a well or receiving area that becomes operatively positioned beneath the nose N (FIG. 2) of the patient after the bite block 10 is inserted into the patient's mouth as described later herein. Notice that the area 50 provides fluid communication to the passageways 36 and 44. This area 50 becomes associated with a patient's nose N, as illustrated in FIGS. 1 and 2, during use of the bite block 10. Notice also that the channels, conduits or passageways 34 and 42 are in fluid communication with the opening 50 defined by the wall 56 which is integrally formed in the bite block 10.

In the illustration being described, the wall 56 is generally arcuate or curved in cross-section along its longitudinal axis as shown in FIGS. 5 and 6. The wall 56 is generally circular or oval shaped, as viewed in FIG. 7, in a cross-section perpendicular to its axis. The opening 50 is in communication with the patient's oral cavity, throat or mouth M. Notice that the wall 56 has an upper area or surface 56a (FIG. 5) that becomes situated in proximity to that patient's upper jaw UJ (FIG. 2) and teeth 58. The wall 56 also has a bottom area or surface 56b that becomes associated with a lower jaw LJ and teeth 59. The wall 56 facilitates retaining the mouth in an open position. This permits, among other things, the patient's mouth M to be retained in an open position so that tubing, instruments, tools, dilators or other items (not shown) may be inserted through the opening 50 and into the throat of the patient.

Figures 9, 10, 11:
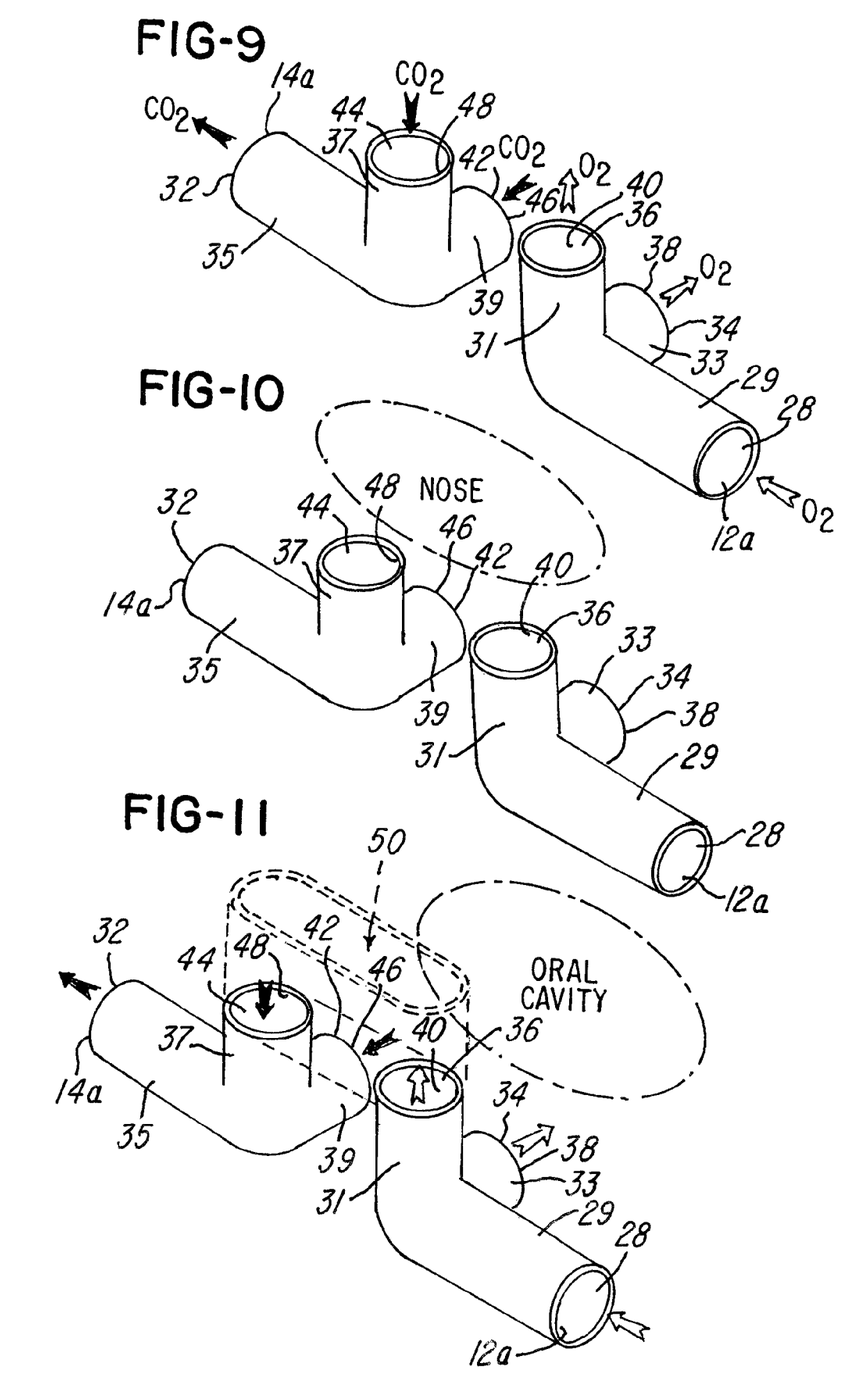
FIGS. 9-11 are simplified diagrammatic representations of a plurality of passageways, flow paths, conduits or channels within the bite block or manifold of FIG. 1.
Figure 12:
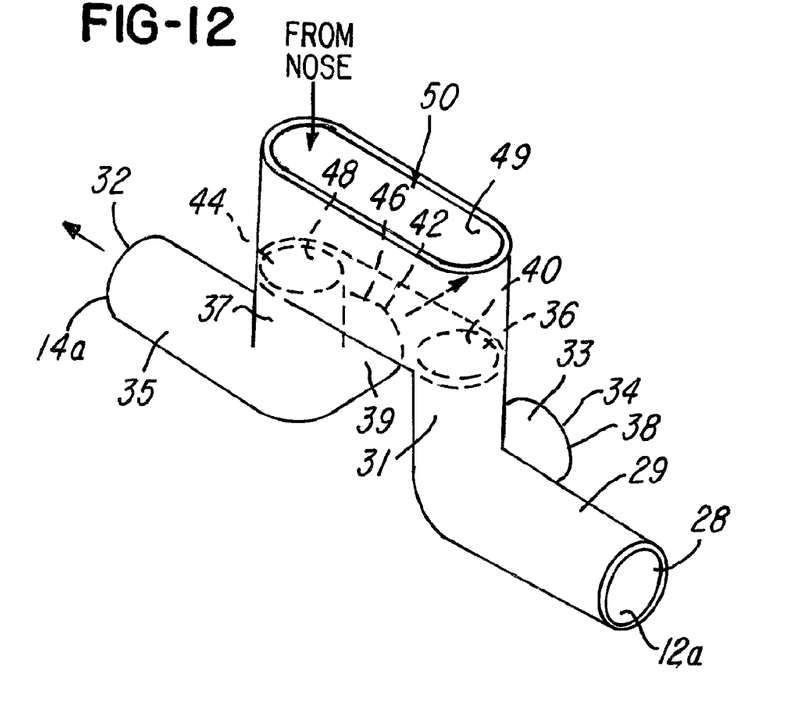
FIG. 12 is a diagrammatic representation of a plurality of passageways, illustrating air being exhaled from a nose of a patient toward a receiving area of the bite block or manifold in FIG. 1.

FIGS. 9 and 10 illustrate that during operation, fluids, such as oxygen, enter conduit 28 from tubing 18 and exits into the patient's mouth M via conduit 34 and toward the patient's nose via conduit 36 for inhaling by the patient. Sampled fluid, such as the patient's exhaled gas or breath (represented by $CO_2$ in FIG. 1), enters or is received in passageways or conduits 42 and 44. The patient's exhale is received in passageway or conduit 32 and received in tube 22 and ultimately received by the monitoring system 20.

FIGS. 9-13 are simplified diagrammatic representations of the bite block 10 of the fluid circuit and passageways in bite block 10 of FIG. 1. The figures illustrate that at least one inlet passageway comprising one or more passageways, ducts or channels 28, 34 and 36 that are connected together and in fluid communication; that is, fluid is free to flow from any of the three ducts into any other of the three ducts (subject, of course, to pressure gradients which may be present). At least one outlet passageway, comprising the plurality of passageways, ducts or channels 32, 42 and 44 are similarly connected together and in fluid communication.

As best illustrated in FIGS. 9-11, note that the first inlet passageway comprises the first leg portion 29 that defines the first passageway, conduit, duct or channel 28, a second leg portion 31 that defines the second passageway, conduit, duct or channel 36 and a third leg portion 33 that defines the third passageway, conduit, duct or channel 34. Note that the first, second and third leg portions are in fluid communication yet their respective axes are not coaxial. Likewise, the at least one outlet passageway comprises the fourth leg portion 35, fifth leg portion 37 and sixth leg portion 39, which define the fourth, fifth and sixth conduits, channels, ducts or passageways 32, 44 and 42, respectively. Note that the fourth leg portion 35, fifth leg portion 37 and sixth leg portion 39 are in fluid communication and also have axes that are not coaxial.

As illustrated diagrammatically by the FIGS. 9-11, the first leg portion 29 defines the passageway 28 that receives fluid, such as oxygen, from the fluid source or supply 16 (FIG. 1) and may deliver it to at least one or both of the passageway, duct or channel 36 defined by second leg portion 31, and passageway, duct or channel 34 defined by third leg portion 33. In the illustration being described, the second and third leg portions 31 and 33 are adapted or arranged to deliver the fluid to at least one or both of the nose and mouth, respectively, of the patient. Although not shown, it should be appreciated that more or fewer outlets or leg portions may be provided. For example, the bite block 10 could be molded to provide a passageway that comprises just leg portions 29 and 31 or 29 and 33 in combination so that the inlet passageway only delivers fluid to the nose or mouth, respectively. In one embodiment, the inlet passageway is defined by walls 12a, 38 and 40 and the outlet passageway is defined by walls 14a, 46 and 48. The walls 12a, 38, 40, 14a, 46 and 48 may be integrally formed onto bite block 10. Although not shown, the inlet and outlet passageways may be provided as a separate assembly. However, in the illustration being described, the bite block 10 comprises the passageway 28 that delivers fluid to both the mouth and the nose of the patient.

Similarly, the at least one outlet passageway may receive fluid from both the mouth and nose of the patient after the bite block 10 is inserted into the patient's mouth. Thus, the fifth leg portion 37 may receive exhaled air, for example, into passageway 44 from the patient's nose, while fluid, such as exhaled air, may be received in the sixth leg portion 39 and passageway 42 from the patient's mouth. As mentioned earlier herein, note that the leg portions 35, 37 and 39 are in fluid communication and have axes that are not coaxial. In one embodiment, the axes of the respective leg portions 29-39 may be situated at angles such that the outlet of the leg portions 31 and 37 are in proximity to the patient's nose, while the outlets of leg portions 33 and 39 become associated with the patient's mouth.

Figure 7:
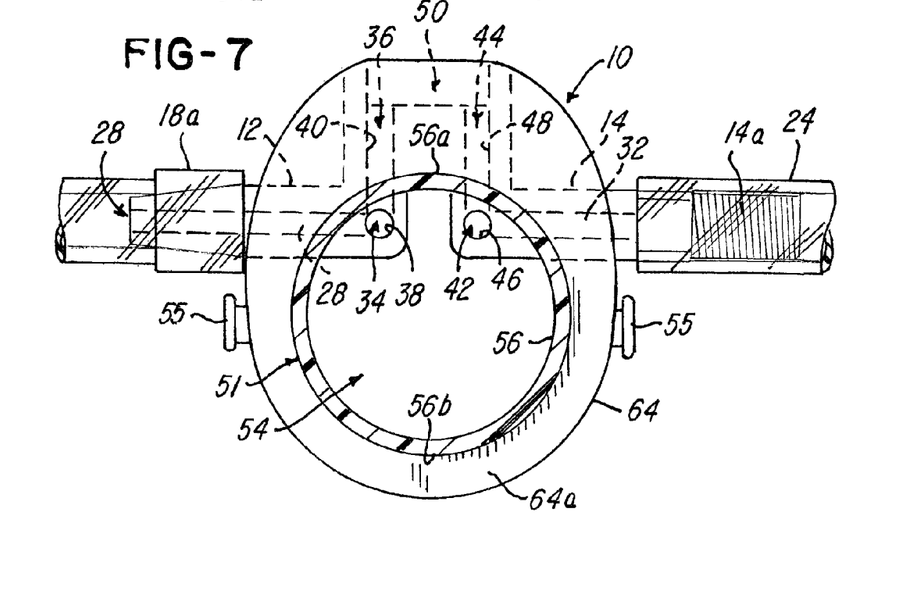
FIG. 7 is a cross-sectional view of the device of FIG. 4, taken in the direction of line 7-7 in FIG. 4.

As shown in FIG. 10, passageways, channels, conduits or ducts 36 and 44 communicate, via the area 50 (FIG. 11), to provide oxygen to one or both nostrils of the patient's nose N (FIG. 1). As mentioned later herein, the passageways or ducts 34 and 42 may define a Y-shaped or star-shaped connection. These passageways, channels, conduits or ducts 36 and 44 are also shown in FIG. 4. As shown in FIGS. 7 and 11, passageways, channels, conduits or ducts 34 and 42 communicate with the patient's mouth, throat or oral cavity. These ducts 34 and 42 are also shown diagrammatically in FIGS. 9-13. Notice that FIG. 2 shows the communication of duct 44 with the nose and duct 42 with the mouth.

The bite block 10 in FIG. 1 may contain at least one or a plurality of molded strap, holders, connectors or ears 55 in FIGS. 1 and 7, to which is attached a band (such as a latex-free band), Velcro® strip or other elastic strap or band 57 (shown in phantom in FIG. 1), which retains the bite block 10 in position to the head of the patient. It should be understood, however, that the bite block 10 may be used with or without straps.

A generally planar wall 64 extends radially from the bottom surface 56b and lies in a plane P that is generally perpendicular to an axis A of said bite block 10. Notice that a first surface 64a abuts the lips L or the teeth 59, or both lips L and teeth 58 and 59, of the patient, and is held in place by the combined action of the lips, teeth, and the band 57 (FIG. 1). A pair of generally opposed, crescent-shaped lip retainer walls or flanges 66a and 66b (FIGS. 2 and 6) are integrally molded onto wall 56 and provides means and apparatus for a bottom lip and a top lip, respectfully of the patient between wall 64 and flanges 66a and 66b.

In operation, the bite block 10 receives incoming oxygen in passageway or duct 28, as illustrated in FIGS. 1 and 9. The incoming oxygen is directed to exit passageways or ducts 34 and 36, which deliver the oxygen to the oral cavity or mouth and nose, respectively, as illustrated diagrammatically in FIGS. 10 and 11. The patient breathes the incoming oxygen, together with ambient air drawn through passageway 54 and area 50 in FIG. 2.

During exhalation, the patient exhales air from the nose, the mouth, or both, as indicated in FIGS. 9-11, part of which may be captured by the passageways, conduits, channels or ducts 42 and 44, respectively. The captured air forms a sample, which is delivered to the passageway 32 (FIGS. 9 and 10) and, thereafter, to line 22 in FIG. 1. As mentioned earlier, line 22 leads to the monitoring system 20 which measures a gas concentration, such as carbon dioxide concentration, in the exhaled air. Concentration generally refers to the amount of carbon dioxide present per unit of exhaled air, in units such as parts per hundred by volume, for example.

A possible source of error in measuring the carbon dioxide concentration will now be discussed. If no oxygen is being delivered from passageway 28 in FIG. 1, then the air sampled through connecting portion 14 and on line 22 will accurately represent the air exhaled from the patient's lungs. However, a possible source of error lies in ambient air which may also enter the connecting portion 14 and line 22. This ambient air can enter passageway 54 in FIG. 2 from the left side of FIG. 5, or it may leak through the interface between the bite block 10 and the patient's cheek or lips. This ambient air may then reach the outlet or sampling port 14 in FIG. 4 via conduit 42, for example, thereby diluting the sample. However, this stray ambient air may be considered insignificant in amount, so that the sampled air in line 22 is considered an accurate representation of the exhaled air in the patient's lungs.

The stray ambient air may be considered insignificant for at least two reasons. One is that the seal between the bite block 10 and the patient's face is considered very good. The bite block 10 provides a tight fit between the patient's lips and the wall 64.

A second reason is that, as explained below, during the exhalation phase of the patient's breathing, exhaled air is moving out of the passageway 54 (i.e., from right to left in FIG. 2), thereby blocking ambient air from entering passageway 54, contrary to the situation considered above.

The situation just discussed presumed that no oxygen was being delivered on line 18 in FIG. 1. If, on the other hand, oxygen is being delivered on line 18 in FIG. 1, then, in theory, the air being exhaled through passageway 54 in FIG. 2 can be diluted by the oxygen delivered through the passageway or duct 34. Also, it is possible that oxygen present in the passageway or duct 44 in FIG. 4, which is intended to reach the nose, can travel to the passageway or duct 36, through the well; opening or area 50, also shown in FIGS. 7 and 11. This dilution, in theory, may cause the carbon dioxide concentration measured by the monitoring system 20 to be incorrectly low.

However, this dilution issue is not seen to be of significance because the monitoring system 20 is capable of detecting low levels of $CO_2$, which provides an indication that the patient is breathing During a medical procedure, it is typically only desired or important to monitor for confirming that the patient is breathing.

Even if oxygen flow is not blocked as in the two approaches just outlined, the structure of the bite block 10 itself tends to block migration of oxygen from the passageways, conduits, channels or ducts 34 and 36 in FIG. 10 to ducts 42 and 44, respectively, during the exhalation cycle. During exhalation, for oxygen exiting conduit 36 in FIG. 12 to reach conduit 32 through area 50, the oxygen must overcome the pressure or flow from the nose, indicated by the dashed arrows. Only a very small amount of oxygen, if any, will successfully overcome this flow and reach conduit 32.

Figure 13:
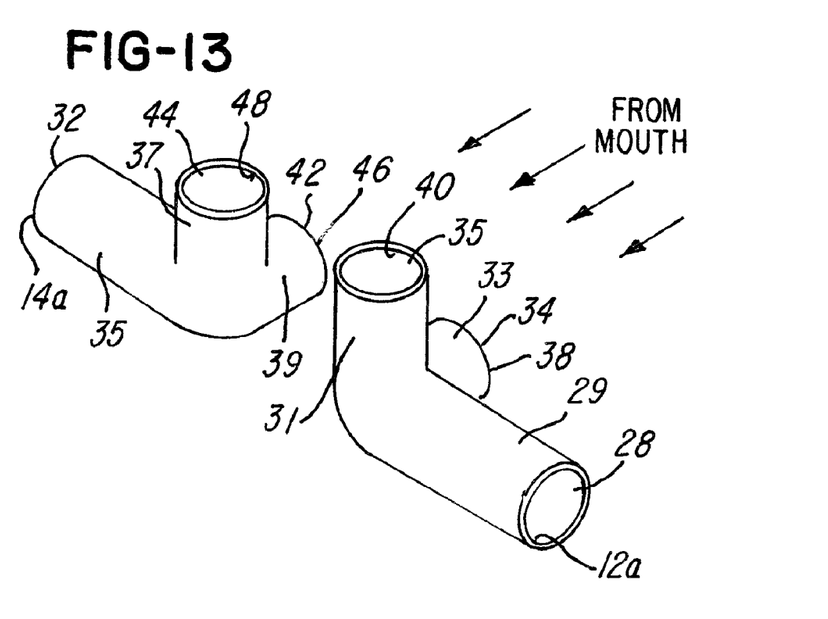
FIG. 13 is a diagrammatic representation of a plurality of passageways, illustrating air being exhaled from the mouth of a patient toward the bite block or manifold in FIG. 1.

Similarly, for oxygen exiting conduit 34 in FIG. 13 to reach conduit 42, it must cross and overcome the exhalation flow indicated by the dashed arrows, analogous to a boat crossing a current in a flowing river. The exhalation flow will drive the oxygen out of passageway 54 (FIG. 2) before the oxygen can make the lateral transit in FIG. 13 from conduit 34 to conduit 42. It should be appreciated that the monitoring system 20 can sense $CO_2$ from either or both the mouth and the nose.

Therefore, the structure, design and placement of the passageways 28, 34, 36 and 32, 44 and 42 is thought to have the advantage of dilution of the sampled gas obtained in conduit 32 by incoming oxygen. Exhaled air tends to drive incoming oxygen away from the sampling conduits 42 and 44.

In addition, another resolution to the dilution issue lies in the fact that the amount of oxygen passing through conduit 28 in FIGS. 9 and 10 is relatively small. Even if all this oxygen is mixed into the exhaled air, thereby diluting the exhaled air, the resulting dilution will be small, but the monitoring system 20 is sensitive enough that it is capable of detecting small amounts of $CO_2$.

Figure 8A:
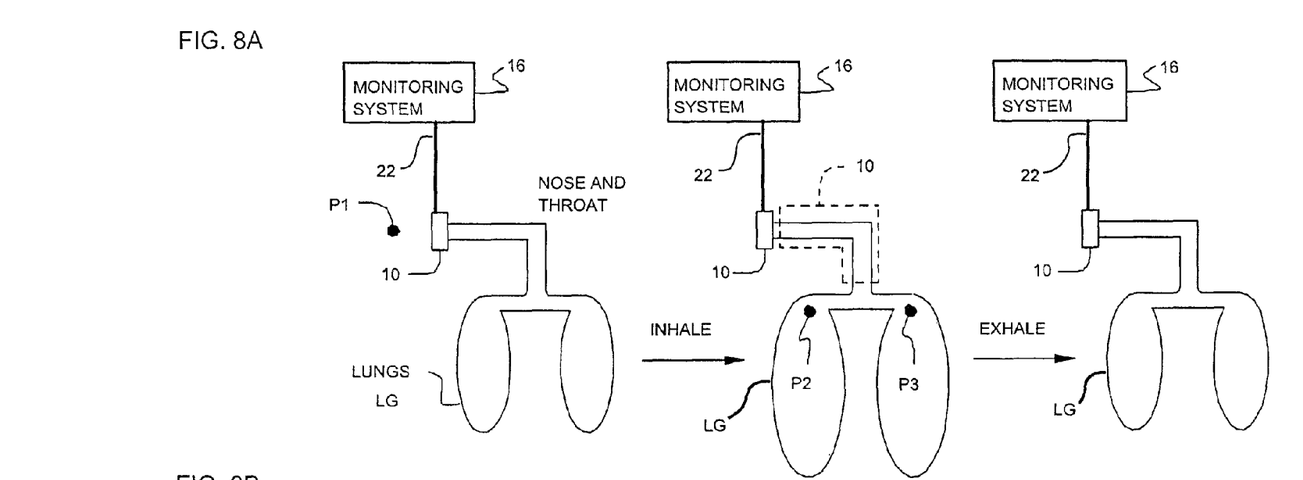
FIG. 8A is a simplified and diagrammatic view providing and explanation of how carbon dioxide measured by the invention may vary during inhalation and exhalation of a patient.
Figure 8B:
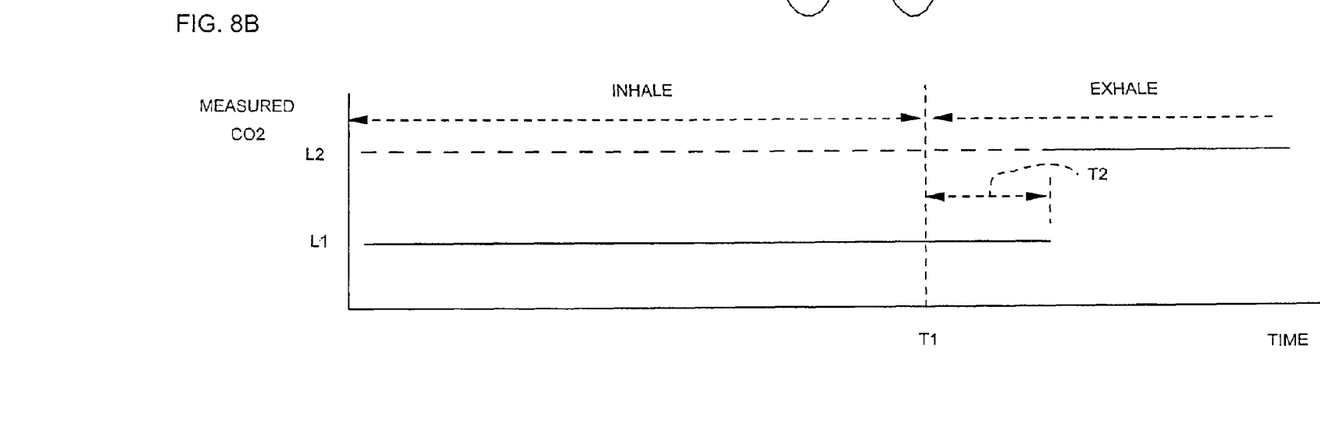
FIG. 8B is a graph illustrating a $CO_2$ versus time of the inhalation and exhalation of a patient.

It is noted that the carbon dioxide concentration, as measured by the present invention, will not be constant, as will be explained with reference to FIGS. 8A and 8B. FIG. 8A figuratively shows one breath cycle: inhalation, wherein the lungs L expand in the illustration, followed by exhalation, wherein the lungs L contract.

During inhalation, the bite block 10 will sample ambient air, that is, air originating from point P1 on the left side of the FIG. 8A. Consequently, the measured carbon dioxide concentration will be that of ambient air, at a first level, such as L1 in the plot shown in FIG. 8B. Inhalation ends at time T1 in the plot.

Then, during exhalation, the air in the mouth, throat, and larynx will be first expelled. This air is indicated by dashed block 70 in FIG. 8B. The carbon dioxide concentration in this air should also equal that of the ambient air because, with respect to this air, no gas exchange has occurred in the lungs. This expulsion occurs for a length of time T2, indicated in the graph shown in FIG. 8B. Measured carbon dioxide concentration remains the same as previous, as indicated.

Then air from the lungs, represented by outgoing air passing points P2 and P3 is expelled. This air contains carbon dioxide from the patient's metabolism, and measured carbon dioxide will increase to a level, such as level L2 as indicated in FIG. 8B.

Therefore, this simplified explanation illustrates that if air is sampled during the full inhalation-exhalation cycle of the patient, measured carbon dioxide concentration will indicate two general levels, which alternate with each other: (1) the level in the ambient air and (2) the level in the patient's lungs. This can be considered by the technician, or apparatus, which adjusts the rate of oxygen flow, based on the carbon dioxide concentration. For example, the technician may use an average value of the two levels L1 and L2 as indicating the relevant carbon dioxide concentration or oxygen level.

In one form of the invention, the monitoring system 20 in FIG. 1 detects whether carbon dioxide concentration (1) rises above a limit, (2) falls below a limit, or (3) both (1) and (2) and, if so, issues a warning signal in response, such as an audible sound or visual alarm. Systems which accomplish this notification or alarm function are known in the art and referred to earlier herein.

In one embodiment, the cross-sectional area of passageway 54 in FIG. 2 is less than the average cross-sectional area of the adult human mouth, held wide open. In one form of the invention, passageway 54 is approximately 22 millimeters as mentioned earlier. However, bite blocks of different sizes can be made for smaller persons, such as infants, or in larger sizes as well, as for large mouths or even for veterinary purposes. Also, more or fewer passageways 32-44 may be provided, and a bite block could be molded with, for example, multiple oxygen or fluid ports and multiple $CO_2$ or exhaust ports for monitoring purposes. Also, multiple ports could be provided for both delivering, for example, oxygen to the patient or for receiving $CO_2$ from the patient if desired.

The bite block can, in one embodiment, comprise a phosphor, photoluminescent or "glow-in-the-dark" material incorporated into or integrally formed as a part of the bite block 10. This is illustrated diagrammatically by the dots D in FIG. 1. In general, phosphor or photoluminescent materials are believed to absorb light, store energy obtained from the light, and then re-emit light over a period of time, in a process which is sometimes called "glowing in the dark." The glow-in-the-dark bite block or bite block 10 can be useful because frequently the patient is present in a dimly lit room, such as an operating room in a hospital. The glow emitted by the luminescent bite block 10 provides assistance to medical technicians, such as providing a circular glowing target (wall 64) to facilitate inserting tubing or other apparatus into the mouth or throat of the patient.

Although not shown, the bite block 10 could be made of any desired color and could be molded with or without the glow-in-the-dark material referred to earlier.

It was stated that the monitoring system 20 in FIG. 1 is used to measure carbon dioxide concentration. The monitoring system 20 may be selected to detect other fluids, such as gases other than $CO_2$.

Because the conduits 28, 34 and 36 in FIGS. 7 and 9-11 meet at a common area 50 or point, they can be said to be "Y-connected," or "star-connected," by analogy to the arms of the letter "Y," the arms of a starfish, or the rays of an asterisk. A similar comment applies to conduits 32, 42 and 44.

It is pointed out that oxygen supply 16 in FIG. 1 need not provide absolutely pure oxygen, but can supply other fluids, such as other gas mixtures. The patient breathes ambient atmospheric air through passageway 54 in FIG. 2. Other apparatus exist which a person may place into the mouth, which contain passages through which the person may breathe air. The mouthpiece of a SCUBA diving apparatus provides an example. However, the SCUBA mouthpiece does not deliver ambient atmospheric air. Similarly, aircraft pilots and astronauts may wear face masks which deliver breathable air, or oxygen. However, many of those masks do not deliver ambient atmospheric air, but air from a stored, pressurized source. Neither of these masks provide a system for diagnosing or diagnostic means or process, such as the monitoring system 20.

During use, the technician or doctor positions the bite block 10 in the mouth of the patient as illustrated in FIGS. 1-2. Before or after, the tubing 18 is connected to inlet port 12 and tubing 22 is connected to passageway 44 as shown in FIG. 1. The oxygen supply 16 and monitoring system 20 are activated. The monitoring system 20 generates information and may provide an audio or visual alarm or signal if no $CO_2$ exhale is detected. The technician or doctor may respond thereto by, among other things, changing the amount of oxygen supplied to the patient, changing an anesthesia or otherwise changing a course of care for the patient.

Advantageously, the bite block 10 is unique in that it provides channel(s) or passageway(s) to supply oxygen to the patient, as well as a system to monitor patient's $CO_2$ level. The bite block 10 is attached to the oxygen supply 16 via the tubing 18. The oxygen travels from the oxygen supply 16 through the tubing 18 and is delivered into the patient's nostrils and mouth M via the opening 50 at the top of the bite block 10 and the sixth conduit 42 on the inside of the bite block 10. When the patient exhales, the $CO_2$ enters the tube 22 attached to the opposite side of the bite block 10 via the fifth conduit 44 at the area 50 as well as the sixth conduit 42 on the inside of the bite block 10, and the $CO_2$ is then monitored by the monitoring system 20. The bite block 10 acts as a channel or manifold to deliver, channel or direct oxygen and $CO_2$. Oxygen is supplied and the $CO_2$ level is monitored by the supply 16 and monitor 20, respectively. The nurse or technician may then read and monitor the systems and care for the patient in response thereto.

Note that, once the bite block 10 is inserted, the integral glow-in-the-dark material D may provide guidance to assist the doctor or technician to locate opening 54, so that tubing, instruments, tools and the like may be inserted.

In one form of the invention, the pressure of oxygen delivered to line 18 in FIG. 1 is equal to that used in ordinary oxygen-assist systems, such as the ambulatory tanks used by people having lung impairment.

Advantageously, the bite block 10 is an integral, one-piece molded construction that provides a manifold for direction both $O_2$ and $CO_2$ as described herein.

While the process and product herein described constitute preferred embodiments of this invention, it is to be understood that the invention is not limited to this precise process and product, and that changes may be made therein without departing from the scope of the invention which is defined in the appended claims.

What is claimed is:

1. A bite block adapted to be situated in a patient's mouth, said bite block comprising:
   an outer flange forming a wall; said wall defining a primary aperture adapted to be in communication with an oral cavity of the patient when said bite block is inserted into said patient's mouth, said bite block engaging the patient's mouth and retaining it in an open position;
   at least one inlet passageway in said wall and in fluid communication with said primary aperture adapted to deliver a first fluid from a fluid source to at least one of a nose or said oral cavity of said patient; and
   at least one outlet passageway in said wall and in fluid communication with said primary aperture adapted to enable a second fluid to be delivered from at least one of said nose or said oral cavity to a fluid monitor;
   wherein said first fluid is received in said primary aperture from said at least one inlet passageway and said second fluid is delivered from said primary aperture to said at least one outlet passageway after said bite block is placed in the patient's mouth;
   wherein said at least one outlet passageway comprises:
   an outlet port defining an outlet passageway for connecting to said fluid monitor;
   a first conduit adapted to become associated with said patient's nose when said bite block is inserted into said patient's mouth; and
   a second conduit adapted to become associated with said oral cavity of said patient when said bite block is inserted into said patient's mouth;
   said outlet port, said first conduit and said second conduit being in fluid communication:
   wherein said at least one inlet passageway comprises:
   an inlet port defining an inlet passageway for connecting to a fluid source;
   a third conduit adapted to become associated with said patient's nose when said bite block is inserted into said patient's mouth; and
   a fourth conduit adapted to become associated with said oral cavity of said patient when said bite block is inserted into said patient's mouth;
   said inlet port, said third conduit and said fourth conduit being in fluid communication; and
   wherein said outer flange comprises a well or receiving area that becomes operatively positioned beneath said patient's nose after said bite block is inserted into said patient's mouth, said well or receiving area being in fluid communication with said first conduit and said third conduit.

2. The bite block as recited in claim 1 wherein said bite block is a one-piece molded construction.

3. The bite block as recited in claim 2 wherein said bite block comprises a phosphor, photoluminescent or glow-in-the-dark material to permit said bite block to glow-in-the-dark.

4. The bite block as recited in claim 1 further comprising:
   an inner flange in generally opposed relation to said outer flange,
   said inner flange adapted to either engage a tongue of said patient or cooperate with said outer flange to provide an area for receiving a lip of said patient.

5. The bite block as recited in claim 1 wherein said at least one inlet passageway and said at least one outlet passageway are arranged in order to facilitate minimizing said first fluid from diluting said second fluid received in said at least one outlet passageway.

6. The bite block as recited in claim 1 wherein said bite block further comprises a generally cylindrical portion defining said primary aperture,
   said at least one inlet passageway being defined by an inlet wall and said at least one outlet passageway being defined by an outlet wall said at least one inlet passageway and said at least one outlet passageway being in said generally cylindrical portion and in fluid communication with said primary aperture.

7. The bite block as recited in claim 1 wherein said first fluid is oxygen.

8. The bite block as recited in claim 1 wherein said second fluid is carbon dioxide.

9. The bite block as recited in claim 1 wherein said outlet passageway is adapted to be associated with a first nostril of said patient and said third conduit adapted to be associated with a second nostril of said patient after said bite block is inserted into said patient's mouth.

10. The bite block as recited in claim 1 wherein said bite block is molded from a thermoplastic material.

11. The bite block as recited in claim 1 wherein said bite block is a one-piece molded connection.

12. The bite block as recited in claim 1 wherein said at least one inlet passageway comprises a first leg portion for coupling to said fluid source and a second leg portion in fluid communication with said first leg portion, said second leg portion having a second leg portion outlet adapted to deliver fluid to said patient's nose.

13. The bite block as recited in claim 12 wherein an axis of said first leg portion is not coaxial with an axis of said second leg portion.

14. The bite block as recited in claim 12 wherein said at least one inlet passageway comprises a third leg portion in fluid communication with said first leg portion, said third leg portion having a third leg portion outlet adapted to deliver fluid to said patient's mouth.

15. The bite block as recited in claim 14 wherein an axis of said first leg portion is not coaxial with an axis of said third leg portion.

16. The bite block as recited in claim 12 wherein said at least one inlet passageway comprises a third leg portion in fluid communication with said first leg portion and said second leg portion, said third leg portion having a third leg portion outlet adapted to deliver fluid to said patient's mouth.

17. The bite block as recited in claim 16 wherein an axis of said first leg portion is not coaxial either an axis of said second leg portion or an axis of said third leg portion.

18. The bite block as recited in claim 1 wherein said at least one outlet passageway comprises a fourth leg portion for coupling to said fluid monitor and a fifth leg portion in fluid communication with said fourth leg portion, said fifth leg portion having a fifth leg portion outlet adapted to receive fluid from said patient's nose.

19. The bite block as recited in claim 18 wherein an axis of said fourth leg portion is not coaxial with an axis of said fifth leg portion.

20. The bite block as recited in claim 18 wherein said at least one outlet passageway comprises a sixth leg portion in fluid communication with said fourth leg portion, said sixth leg portion having a sixth leg portion outlet adapted to receive fluid from said patient's mouth.

21. The bite block as recited in claim 20 wherein an axis of said fourth leg portion is not coaxial with an axis of said sixth leg portion.

22. The bite block as recited in claim 18 wherein said at least one outlet passageway comprises a sixth leg portion in fluid communication with said fourth leg portion and said fifth leg portion, said sixth leg portion having a sixth leg portion outlet adapted to receive fluid from said patient's mouth.

23. The bite block as recited in claim 22 wherein an axis of said fourth leg portion is not coaxial either an axis of said fifth leg portion or an axis of said sixth leg portion.

24. The bite block as recited in claim 12 wherein said at least one outlet passageway comprises a fourth leg portion for coupling to said fluid monitor and a fifth leg portion in fluid communication with said fourth leg portion, said fifth leg portion having a fifth leg portion outlet adapted to receive fluid from said patient's nose.

25. The bite block as recited in claim 24 wherein said at least one outlet passageway comprises a sixth leg portion in fluid communication with said fourth leg portion and said fifth leg portion, said sixth leg portion having an sixth leg portion outlet adapted to receive fluid from said patient's mouth.

26. The bite block as recited in claim 1 wherein said at least one inlet passageway being defined by an inlet wall and said at least one outlet passageway being defined by an outlet wall that is integrally molded onto said bite block.

27. A monitoring system comprising:
a bite block adapted to be inserted into a patient's mouth, said bite block having an inlet port in communication with at least one inlet passageway and an outlet port in communication with at least one outlet passageway;
an oxygen supply coupled to said inlet port; and
a carbon dioxide monitor coupled to said outlet port;
said bite block providing a manifold for delivering oxygen from said inlet port to at least one of a nose or an oral cavity of said patient and for capturing exhaled air from said patient for delivery through said at least one outlet passageway to said carbon dioxide monitor;
said bite block further comprising an outer flange forming a wall defining a primary aperture, said at least one inlet passageway and said at least one outlet passageway being in said wall and in fluid communication with said primary aperture so that said oxygen and said exhaled air may be delivered to and received from, respectively, said primary aperture;
said bite block retaining said patient's mouth in an open position after said bite block is situated in said patient's mouth;
wherein said at least one outlet passageway comprises:
an outlet port defining an outlet passageway for connecting to a fluid monitor;
a first conduit adapted to become associated with said patient's nose when said bite block is inserted into said patient's mouth; and
a second conduit adapted to become associated with said oral cavity of said patient when said bite block is inserted into said patient's mouth;
said outlet port, said first conduit and said second conduit being in fluid communication;
wherein at least one inlet passageway comprises:
an inlet port defining an inlet passageway for connecting to a fluid source;
a third conduit adapted to become associated with said patient's nose when said bite block is inserted into said patient's mouth; and
a fourth conduit adapted to become associated with said oral cavity of said patient when said bite block is inserted into said patient's mouth;
said inlet port, said third conduit and said fourth conduit being in fluid communication; and
wherein said outer flange comprises a well or receiving area that becomes operatively positioned beneath said patient's nose after said bite block is inserted into said patient's mouth, said well or receiving area being in fluid communication with said first conduit and said third conduit.

28. The monitoring system as recited in claim 27 wherein said primary aperture is adapted to be in communication with said oral cavity of said patient when said bite block is inserted into said patient's mouth, said bite block further comprising:
said inlet passageway adapted to deliver said oxygen from an oxygen source to at least one of said nose or said oral cavity of said patient;
said outlet passageway adapted to enable carbon dioxide to be delivered from at least one of said nose or said oral cavity to said carbon dioxide monitor.

29. The bite block as recited in claim 27 wherein said bite block is a one-piece molded construction.

30. The bite block as recited in claim 27 wherein said bite block comprises a phosphor, photoluminescent or glow-in-the-dark material integrally formed therein.

31. The bite block as recited in claim 29 further comprising:
 an inner flange in generally opposed relation to said outer flange,
 said inner flange adapted to cooperate with said outer flange to provide an area for receiving a lip of said patient.

32. The bite block as recited in claim 27 wherein said inlet passageway and said outlet passageway are arranged in order to facilitate minimizing said oxygen from diluting said air received in said outlet passageway.

33. The bite block as recited in claim 27 wherein said bite block further comprises a generally cylindrical portion defining a primary aperture,
 said inlet passageway and said outlet passageway being in a generally opposed relationship.

34. The bite block as recited in claim 27 wherein said first conduit is adapted to be associated with a first nostril of said patient and said third conduit adapted to be associated with a second nostril of said patient after said bite block is inserted into said patient's mouth.

35. A medical apparatus, comprising:
 a) an appliance which is adapted to hold open a patient's mouth, comprising:
  i) an outer flange forming a wall defining a passage through which said patient can breathe ambient atmospheric air and an instrument may be inserted therein;
  ii) a first conduit defining at least one inlet passageway effective to deliver oxygen from an external supply to said passage, and
 b) a second conduit defining at least one outlet passageway which:
  i) connects to the passage, and
  ii) is adapted to define a passageway for receiving some exhaled air from the passage and delivering said exhaled air from said passage to a gas-monitoring apparatus;
 wherein said at least one outlet passageway comprises:
 an outlet port defining said at least one outlet passageway for connecting to a fluid monitor;
 said first conduit adapted to become associated with a patient's nose when a bite block is inserted into said patient's mouth; and
 said second conduit adapted to become associated with an oral cavity of said patient when said bite block is inserted into said patient's mouth;
 said outlet port, said first conduit and said second conduit being in fluid communication;
 wherein said at least one inlet passageway comprises:
 an inlet port defining said at least one inlet passageway for connecting to a fluid source;
 a third conduit adapted to become associated with said patient's nose when said bite block is inserted into said patient's mouth; and
 a fourth conduit adapted to become associated with said oral cavity of said patient when said bite block is inserted into said patient's mouth;
 said inlet port, said third conduit and said fourth conduit being in fluid communication; and
 wherein said outer flange comprises a well or receiving area that becomes operatively positioned beneath said patient's nose after said bite block is inserted into said patient's mouth, said well or receiving area being in fluid communication with said first conduit and said third conduit.

36. The medical apparatus according to claim 35 and further comprising phosphor or photoluminescent material, which causes said apparatus to emit light or glow in the dark.

37. A medical apparatus, comprising:
 a) a body having an outer flange that provides a wall that defines a passage through which a patient can breathe ambient atmospheric air;
 b) a first conduit that provides at least one inlet passageway which connects said passage with an inlet port for receiving oxygen; and
 c) a second conduit that provides at least one outlet passageway which connects said passage with an outlet port for delivering exhaled air to a gas monitoring apparatus;
 said body holding a patient's mouth open after it is inserted into said patient's mouth so that an instrument can be inserted into said passage;
 wherein said at least one outlet passageway comprises:
 said outlet port defining said at least one outlet passageway for connecting to a fluid monitor;
 said first conduit adapted to become associated with a patient's nose when a bite block is inserted into said patient's mouth; and
 said second conduit adapted to become associated with an oral cavity of said patient when said bite block is inserted into said patient's mouth;
 said outlet port, said first conduit and said second conduit being in fluid communication;
 wherein said at least one inlet passageway comprises:
 said inlet port defining said at least one inlet passageway for connecting to a fluid source;
 a third conduit adapted to become associated with said patient's nose when said bite block is inserted into said patient's mouth; and
 a fourth conduit adapted to become associated with said oral cavity of said patient when said bite block is inserted into said patient's mouth;
 said inlet port, said third conduit and said fourth conduit being in fluid communication; and
 wherein said outer flange comprises a well or receiving area that becomes operatively positioned beneath said patient's nose after said bite block is inserted into said patient's mouth, said well or receiving area being in fluid communication with said first conduit and said third conduit.

38. The medical apparatus according to claim 37 wherein, during operation, said inlet port is connected to a source of oxygen that provides oxygen to said patient.

39. A medical apparatus comprising:
 a) an appliance which
  i) holds open a patient's mouth, and
  ii) comprises an outer flange that forms a wall that provides a passage through which said patient can breathe ambient atmospheric air normally;
 b) a manifold, comprising:
  i) a first set of conduits that define at least one outlet passageway comprising:
   A) a first conduit leading to an outlet port,
   B) a second conduit leading to a patient's nose, and
   C) a third conduit leading to said passage;
  ii) a second set of conduits that define at least one inlet passageway comprising:
   A) a fourth conduit leading to an inlet port,
   B) a fifth conduit leading to the patient's nose, and
   C) a sixth conduit leading to said passage;

said first, second and third conduits all being in fluid communication and said fourth, fifth and sixth conduits all being in fluid communication;

said passage receiving said ambient atmospheric air and a first fluid from said sixth conduit while permitting exhaled air to be collected or received in said second or third conduit;

wherein said outer flange comprises a well or receiving area that becomes operatively positioned beneath said patient's nose after said appliance is inserted into said patient's mouth, said well or receiving area being in fluid communication with said second conduit and said fourth conduit.

40. The medical apparatus according to claim 39 wherein said fourth conduit is in fluid communication with and provides oxygen to said fifth and sixth conduits when connected to an oxygen supply.

41. The medical apparatus according to claim 39 wherein said first conduit is in fluid communication with said second and third conduits to receive a sample of exhaled air from at least one of said second or said third conduit.

42. The medical apparatus according to claim 41 and further comprising:

a monitoring system connected to the first conduit, which measures concentration of a carbon dioxide in air exhaled by said patient.

43. A method, comprising the steps of:
a) situating a bite block within a patient's mouth which provides a passage through which said patient can breathe ambient atmospheric air and a surgical instrument may be placed, said bite block engaging said patient's mouth and retaining said patient's mouth in an open position;
b) delivering oxygen to the passage for inhalation by said patient;
c) detecting concentration of a gas in said patient's exhaled air;
said bite block having at least one passageway for delivering said oxygen to said passage and at least one second passageway for receiving exhaled air from at least one of said passage or from an area associated with said patient's nose; and
d) using a bite block comprising:
an outer flange forming a wall; said wall defining a primary aperture adapted to be in communication with an oral cavity of the patient when said bite block is inserted into said patient's mouth, said bite block engaging the patient's mouth and retaining it in an open position;
at least one inlet passageway in said wall and in fluid communication with said primary aperture adapted to deliver a first fluid from a fluid source to at least one of a nose or said oral cavity of said patient; and
at least one outlet passageway in said wall and in fluid communication with said primary aperture adapted to enable a second fluid to be delivered from at least one of said nose or said oral cavity to a fluid monitor;
wherein said first fluid is received in said primary aperture from said at least one inlet passageway and said second fluid is delivered from said primary aperture to said at least one outlet passageway after said bite block is placed in the patient's mouth;
wherein at least one outlet passageway comprises:
an outlet port defining an outlet passageway for connecting to a fluid monitor;
a first conduit adapted to become associated with said patient's nose when said bite block is inserted into said patient's mouth; and
a second conduit adapted to become associated with an oral cavity of said patient when said bite block is inserted into said patient's mouth;
said outlet port, said first conduit and said second conduit being in fluid communication;
wherein at least one inlet passageway comprises:
an inlet port defining an inlet passageway for connecting to a fluid source;
a third conduit adapted to become associated with said patient's nose when said bite block is inserted into said patient's mouth; and
a fourth conduit adapted to become associated with said oral cavity of said patient when said bite block is inserted into said patient's mouth;
said inlet port, said third conduit and said fourth conduit being in fluid communication; and
wherein said outer flange comprises a well or receiving area that becomes operatively positioned beneath said nose of said patient after said bite block is inserted into said patient's mouth, said well or receiving area being in fluid communication with said first conduit and said third conduit.

44. The method according to claim 43 wherein a carbon dioxide concentration is detected during said detecting step.

45. The method according to claim 43 wherein said bite block comprises a plurality of passageways to perform said delivering and detecting steps.

46. A medical apparatus, comprising:
a) an appliance which is adapted to hold open a patient's mouth, which comprises an outer flange comprising a wall that defines a passage through which said patient can breathe ambient atmospheric air and an instrument may be inserted;
b) a conduit in said appliance which delivers oxygen to at least one of said patient's mouth or nose; and
c) a sampling conduit which samples air exhaled by said patient from at least one of said patient's nose or mouth;
said appliance comprising said wall defining said passage, at least one inlet passageway and at least one outlet passageway being in said appliance so that said oxygen and exhaled air may be delivered to and received from, respectively, said passage;
said appliance retaining said patient's mouth open after said appliance is placed in said patient's mouth;
wherein at least one outlet passageway comprises:
an outlet port defining an outlet passageway for connecting to a fluid monitor;
a first conduit adapted to become associated with said patient's nose when said appliance is inserted into said patient's mouth; and
a second conduit adapted to become associated with an oral cavity of said patient when said appliance is inserted into said patient's mouth;
said outlet port, said first conduit and said second conduit being in fluid communication;
wherein said at least one inlet passageway comprises:
an inlet port defining said at least one inlet passageway for connecting to a fluid source;
a third conduit adapted to become associated with said patient's nose when said appliance is inserted into said patient's mouth; and
a fourth conduit adapted to become associated with said oral cavity of said patient when said appliance is inserted into said patient's mouth;
said inlet port, said third conduit and said fourth conduit being in fluid communication; and wherein said outer flange comprises a well or receiving area that becomes operatively positioned beneath said patient's nose after said appliance is inserted into said patient's mouth, said well or receiving area being in fluid communication with said first conduit and said third conduit.

47. The medical apparatus according to claim 46 wherein exhaled air forms a gas stream which oxygen exiting said fourth conduit must cross in order to reach said sampling conduit.

48. A bite block comprising:
a body having an outer flange that comprises a wall that provides a primary passageway, said wall being adapted to hold a patient's mouth open after said body is placed in said patient's mouth and also having a plurality of conduits, said plurality of conduits comprising at least one inlet passageway adapted to be coupled to an oxygen source and receive oxygen and direct said oxygen to at least one of a patient's nose or mouth; and
at least one outlet passageway being adapted to be coupled to a monitor and to receive exhaled air from at least one of said patient's nose or throat;
said primary passageway being adapted to receive at least one instrument;
wherein said at least one outlet passageway comprises:
an outlet port defining said at least one outlet passageway for connecting to a fluid monitor;
a first conduit adapted to become associated with said patient's nose when said bite block is inserted into said patient's mouth; and
a second conduit adapted to become associated with an oral cavity of said patient when said bite block is inserted into said patient's mouth;
said outlet port, said first conduit and said second conduit being in fluid communication;
wherein said at least one inlet passageway comprises:
an inlet port defining said at least one inlet passageway for connecting to a fluid source;
a third conduit adapted to become associated with said patient's nose when said bite block is inserted into said patient's mouth; and
a fourth conduit adapted to become associated with said oral cavity of said patient when said bite block is inserted into said patient's mouth;
said inlet port, said third conduit and said fourth conduit being in fluid communication; and
wherein said outer flange comprises a well or receiving area that becomes operatively positioned beneath said patient's nose after said bite block is inserted into said patient's mouth, said well or receiving area being in fluid communication with said first conduit and said third conduit.

49. The bite block according to claim 48 wherein said body is a one-piece molded construction and said plurality of conduits comprise one inlet port and one monitor port integrally formed in said one-piece body.

50. The bite block according to claim 49 wherein said plurality of conduits comprises a plurality of oxygen delivery ports in fluid communication with said inlet port and a plurality of passageways in fluid communication with said monitor port.

51. The bite block according to claim 48 wherein said at least one outlet passageway comprises a plurality of conduits adapted to receive exhaled carbon dioxide from both said patient's nose and throat.

52. The bite block according to claim 51 wherein said at least one outlet passageway comprises a first channel associated with said patient's nose and a second channel associated with said patient's mouth, said first and second channels being in fluid communication with each other and with a third channel adapted to be coupled to a monitoring system.

53. A medical apparatus for use in a patient comprising:
a bite block for retaining the patient's mouth in an open position; and
supply and monitoring means for providing oxygen to said patient through a primary aperture defined by a wall integral with an outer flange in said bite block and for monitoring exhaled air from said patient;
said bite block comprising a plurality of passageways for directing said oxygen into said primary aperture and for sampling the patient's exhaled air from said primary aperture or from an area associated with said patient's nose; said plurality of passageways comprising at least one inlet passageway and at least one outlet passageway;
said primary aperture being adapted to receive an instrument while said plurality of passageways simultaneously permit delivery of oxygen and sampling of the patient's exhaled air through said plurality of passageways;
wherein said at least one outlet passageway comprises:
an outlet port defining said at least one outlet passageway for connecting to a fluid monitor;
a first conduit adapted to become associated with said patient's nose when said bite block is inserted into said patient's mouth; and
a second conduit adapted to become associated with an oral cavity of said patient when said bite block is inserted into said patient's mouth;
said outlet port, said first conduit and said second conduit being in fluid communication;
wherein said at least one inlet passageway comprises:
an inlet port defining said at least one inlet passageway for connecting to a fluid source;
a third conduit adapted to become associated with said patient' nose when said bite block is inserted into said patient's mouth; and
a fourth conduit adapted to become associated with said oral cavity of said patient when said bite block is inserted into said patient's mouth;
said inlet port, said third conduit and said fourth conduit being in fluid communication; and
wherein said outer flange comprises a well or receiving area that becomes operatively positioned beneath said patient's nose after said bite block is inserted into said patient's mouth, said well or receiving area being in fluid communication with said first conduit and said third conduit.

54. The medical apparatus according to claim 53 wherein said bite block is an integral, one-piece molded construction.

55. A bite block comprising:
a body having an outer flange forming a wall surrounding a primary opening for retaining a patient's mouth in an open position, said body having a plurality of passageways for delivering oxygen to said patient and for receiving exhaled air from said patient after the body is inserted into said patient's mouth; and
a photoluminous or phosphorous material integrally formed in said body to make said outer flange luminescent;
said body defining a primary passage through which an instrument may be inserted into the patient during a surgical procedure and simultaneously permitting delivery of oxygen and sampling of the patient's exhaled air through said plurality of passageways; said plurality of passageways comprising at least one inlet passageway and at least one outlet passageway;

said at least one inlet passageway in said wall and in fluid communication with said primary passage adapted to deliver a first fluid from a fluid source to at least one of a nose or an oral cavity of said patient; and said at least one outlet passageway in said wall and in fluid communication with said primary passage adapted to enable a second fluid to be delivered from at least one of said nose or said oral cavity to a fluid monitor;

wherein said first fluid is received in said primary passage from said at least one inlet passageway and said second fluid is delivered from said primary passage to said at least one outlet passageway after said bite block is placed in the patient's mouth;

wherein said at least one outlet passageway comprises:
an outlet port defining said at least one outlet passageway for connecting to said fluid monitor;
a first conduit adapted to become associated with said patient's nose when said bite block is inserted into said patient's mouth; and
a second conduit adapted to become associated with said oral cavity of said patient when said bite block is inserted into said patient's mouth;
said outlet port, said first conduit and said second conduit being in fluid communication;

wherein said at least one inlet passageway comprises:
an inlet port defining said at least one inlet passageway for connecting to a fluid source;
a third conduit adapted to become associated with said patient's nose when said bite block is inserted into said patient's mouth; and
a fourth conduit adapted to become associated with said oral cavity of said patient when said bite block is inserted into said patient's mouth;
said inlet port, said third conduit and said fourth conduit being in fluid communication; and
wherein said outer flange comprises a well or receiving area that becomes operatively positioned beneath said patient's nose after said bite block is inserted into said patient's mouth, said well or receiving area being in fluid communication with said first conduit and said third conduit.

56. The bite block as recited in claim 55 wherein said body comprises:
an oxygen passageway for delivering oxygen to at least one of a patient's nose or mouth;
a monitoring passageway from delivering CO2 from at least one of said patient's nose or mouth to a monitoring system.

57. A bite block comprising:
a body adapted to define a plurality of conduits, said plurality of conduits comprising:
at least one inlet conduit in a wall and in fluid communication with a primary aperture adapted to deliver a first fluid from a fluid source to at least one of a nose or an oral cavity of a patient;
at least one outlet conduit in said wall and in fluid communication with said primary aperture adapted to enable a second fluid to be delivered from at least one of said nose or said oral cavity to a fluid monitor;
said at least one outlet conduit comprising an outlet adapted to be coupled to a monitor to receive exhaled fluid from at least one of said patient's nose or throat; and
said at least one outlet conduit being adapted to capture exhaled air from at least one of said patient's nose or mouth after said bite block is situated in said patient's mouth during a surgical procedure, said bite block having an outer flange comprising a primary wall for defining a primary passage with said at least one outlet conduit and adapted to receive a surgical instrument after said body is placed in said patient's mouth;

wherein at least one outlet conduit comprises:
an outlet port defining an outlet conduit for connecting to a fluid monitor;
a first conduit adapted to become associated with said patient's nose when said bite block is inserted into said patient's mouth; and a second conduit adapted to become associated with an oral cavity of said patient when said bite block is inserted into said patient's mouth;
said outlet port, said first conduit and said second conduit being in fluid communication;

wherein said at least one inlet conduit comprises:
an inlet port defining an inlet conduit for connecting to a fluid source;
a third conduit adapted to become associated with said patient's nose when said bite block is inserted into said patient's mouth; and
a fourth conduit adapted to become associated with said oral cavity of said patient when said bite block is inserted into said patient's mouth;
said inlet port, said third conduit and said fourth conduit being in fluid communication; and
wherein said wall comprises a well or receiving area that becomes operatively positioned beneath said nose of said patient after said bite block is inserted into said patient's mouth, said well or receiving area being in fluid communication with said first conduit and said third conduit.

58. The bite block according to claim 57 wherein said inlet port has a tapered inlet for coupling to an oxygen source.

59. The bite block according to claim 58 wherein said body is a one-piece molded construction and said at least one inlet conduit comprises and inlet port and said at least one outlet conduit comprises a monitor port, said inlet port and said monitor port being integrally formed in said one-piece body.

60. The bite block according to claim 58 wherein said at least one inlet conduit comprises a plurality of oxygen delivery ports in fluid communication with said at least one inlet conduit and said at least one outlet conduit comprises a plurality of receiving ports in fluid communication with said at least one outlet conduit.

61. The bite block according to claim 57 wherein said at least one outlet conduit comprises a plurality of conduits adapted to receive exhaled air from both said patient's nose and throat.

62. The bite block according to claim 61 wherein at least one outlet port is adapted to be coupled to a hose of a monitoring system.

63. The medical apparatus as recited in claim 39 wherein said second and fifth conduits are in fluid communication with a common area associated with the patient's nose.

64. A bite block for a patient, comprising:
a) a tube, which provides
i) an outer flange for providing a wall that defines an internal passage for entry of surgical instruments and movement of inhaled and exhaled air, and
ii) an external surface which
A) is received by a patient's mouth to hold the patient's mouth open and to position said internal passage generally centrally in the patient's mouth, and B) which cooperates with the patient's mouth so that exhaled air may pass through said internal passage;
b) a manifold, that is
   i) integral with said tube, and
   ii) has an aperture positioned in opposed relationship to a patient's nose when the tube is situated between the patient's upper and lower teeth or gums;
c) an oxygen line that feeds oxygen to said manifold which delivers said oxygen to said internal passage and said aperture; and
d) a sampling conduit that takes samples of exhaled air from the patient from at least one of said aperture or said internal passage;
wherein said manifold enables exhaled air from said patient's mouth to mix with exhaled air from said patient's nose, ambient air or said oxygen that is fed from said sampling conduit to enter said internal passage and said aperture;
said tube comprising:
an outlet port defining said sampling conduit for connecting to a fluid monitor;
a first conduit in communication with said manifold and adapted to become associated with said patient's nose when said bite block is inserted into said patient's mouth; and
a second conduit adapted to become associated with an oral cavity of said patient when said bite block is inserted into said patient's mouth;
said outlet port, said first conduit and said second conduit being in fluid communication;
wherein said tube further comprises:
an inlet port defining an inlet passageway for connecting to a fluid source;
a third conduit adapted to become associated with said patient's nose when said bite block is inserted into said patient's mouth; and
a fourth conduit adapted to become associated with said oral cavity of said patient when said bite block is inserted into said patient's mouth;
said inlet port, said third conduit and said fourth conduit being in fluid communication; and
wherein said tube comprises a well or receiving area that becomes operatively positioned beneath said patient's nose after said bite block is inserted into said patient's mouth, said well or receiving area being in fluid communication with said first conduit and said third conduit.

65. The bite block according to claim 64, in which oxygen from said oxygen line must make a crossing across said internal passage in order to reach said sampling conduit, and exhaled air entrains oxygen present within said internal passage, thereby facilitating preventing the crossing so that exhaled air carries the entrained oxygen into said ambient air surrounding the patient.

* * * * *